(12) United States Patent
Chuang et al.

(10) Patent No.: US 8,119,067 B2
(45) Date of Patent: Feb. 21, 2012

(54) AUTOMATIC PHYSIOLOGICAL ASSAY DEVICE

(75) Inventors: Tsung-Kai Chuang, Tainan County (TW); Chien-Ho Chuang, Kaohsiung (TW); Jiann-Hua Wang, Taipei (TW)

(73) Assignee: Kaiwood Technology Co., Ltd., Hsin-Shi, Tainan County (TW)

( * ) Notice: Subject to any disclaimer, the term of this patent is extended or adjusted under 35 U.S.C. 154(b) by 130 days.

(21) Appl. No.: 12/651,773

(22) Filed: Jan. 4, 2010

(65) Prior Publication Data

US 2011/0165036 A1      Jul. 7, 2011

(51) Int. Cl.
*G01N 21/00*        (2006.01)
(52) U.S. Cl. .................................................. 422/82.05
(58) Field of Classification Search ............... 422/82.05
See application file for complete search history.

(56) References Cited

U.S. PATENT DOCUMENTS

| 4,099,921 | A | * | 7/1978 | Allington | 422/67 |
| 4,719,087 | A | * | 1/1988 | Hanaway | 422/551 |
| 5,536,471 | A | * | 7/1996 | Clark et al. | 422/63 |

* cited by examiner

*Primary Examiner* — Bobby Ramdhanie
(74) *Attorney, Agent, or Firm* — Morris Manning & Martin LLP; Tim Tingkang Xia, Esq.

(57) ABSTRACT

An automatic physiological assay device analyzes light reflected by an assay device and prevents ambient light from interfering with the assay device. The automatic physiological assay device in accordance with the present invention comprises a chassis, an assay device connector assembly, an assay device and a light detecting device. The chassis comprises closed bottom, multiple sidewalls, an inner cavity, an open top and a removable top cover. The assay device connector assembly is mounted slidably through a sidewall and comprises an outer end, two sides and a cover. The cover is mounted on the outer end, seals the sidewall and keeps ambient light away from the assay device. The light detecting device is mounted in the inner cavity and on top edges of guides adjacent the assay device connector assembly.

4 Claims, 5 Drawing Sheets

AUTOMATIC PHYSIOLOGICAL ASSAY DEVICE

FIELD OF THE INVENTION

The invention is an automatic physiological assay device that reflects light from a sample, analyzes color of the light reflected from the sample and prevents ambient light from entering the physiological assay device.

BACKGROUND OF THE INVENTION

Diseases and conditions often affect people's health, and tests need to be performed to determine the existence and severity of the disease or condition. Conventional test methods use an assay device such as a biomedical test strip to test specimens such as blood, saliva or urine. The assay device is manufactured with an antibody-antigen reaction substance and changes color to present a test result. The antibody-antigen reaction substance may be a probe protein corresponding to a target protein and is mounted on the biomedical test strip. The protein probe bonds to the target protein and changes color when the specimen containing the target protein is biomedical test strip. Consequently, the test result is determined by variation in color of the biomedical test strip.

Many years ago, people observed color variation of the biomedical test strip to determine the test results. However, precision of the test result depended on accuracy of an individual's observation, and inaccuracy of test results were not uncommon.

Therefore, light detectors such as photo diodes, complementary metal-oxide-semiconductors and charge-coupled devices are used now in assay devices to detect changes in color of light to obtain consistent test results.

A conventional automatic assay device was developed to overcome the inconsistency of human observation and comprises an assay device and a biomedical test strip. The assay device has a top surface, a slot and a light detector. The slot is formed in the top surface of the assay device. The light detector is mounted in the slot. The biomedical test strip is mounted removably in the slot over the light detector. However, ambient light may shine on the light detector and cause erratic results.

SUMMARY OF THE INVENTION

The main objective of the present invention is to provide an automatic physiological assay device that accurately measures light reflected from a biomedical detector and prevents ambient light from distorting the results.

An automatic physiological assay device in accordance with the present invention comprises a chassis, an assay device connector assembly, an assay device and a light detecting device. The chassis comprises closed bottom, multiple sidewalls, an inner cavity, an open top and a removable top cover. The assay device connector assembly is mounted slidably through a sidewall and comprises an outer end, two sides and a cover. The cover is mounted on the outer end, seals the sidewall and keeps ambient light away from the assay device. The light detecting device is mounted in the inner cavity and on top edges of guides adjacent the assay device connector assembly.

DETAILED DESCRIPTION OF THE PRESENT INVENTION

Figure 1:
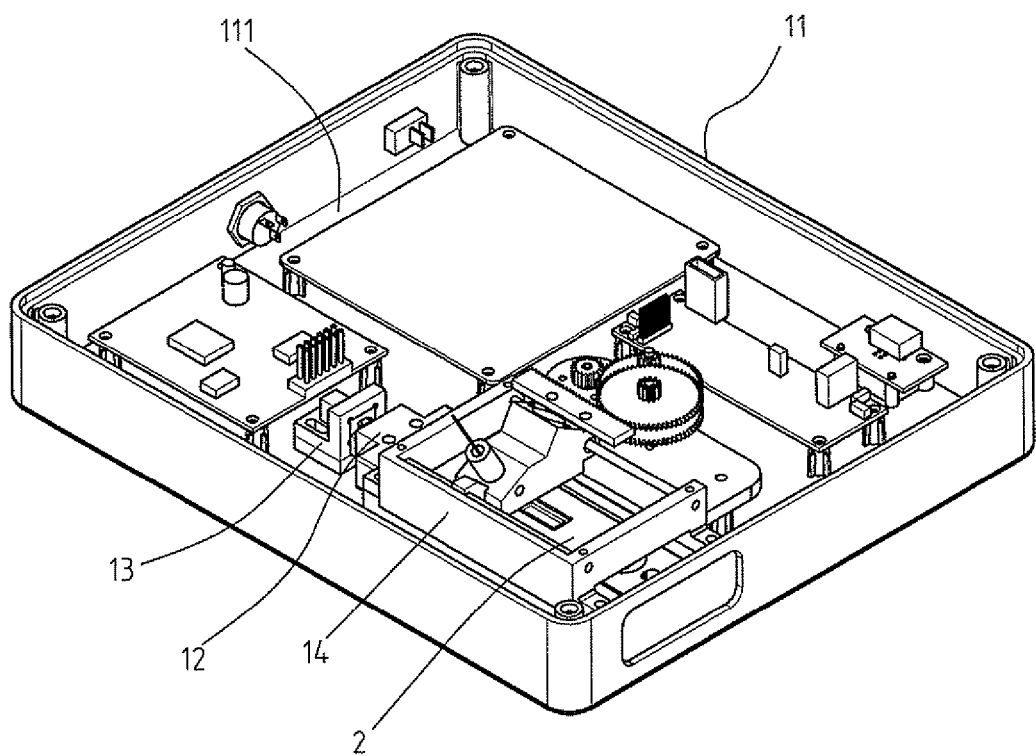
FIG. 1 is a perspective view of an automatic physiological assay device in accordance with the present invention with its top cover removed.
Figure 2:
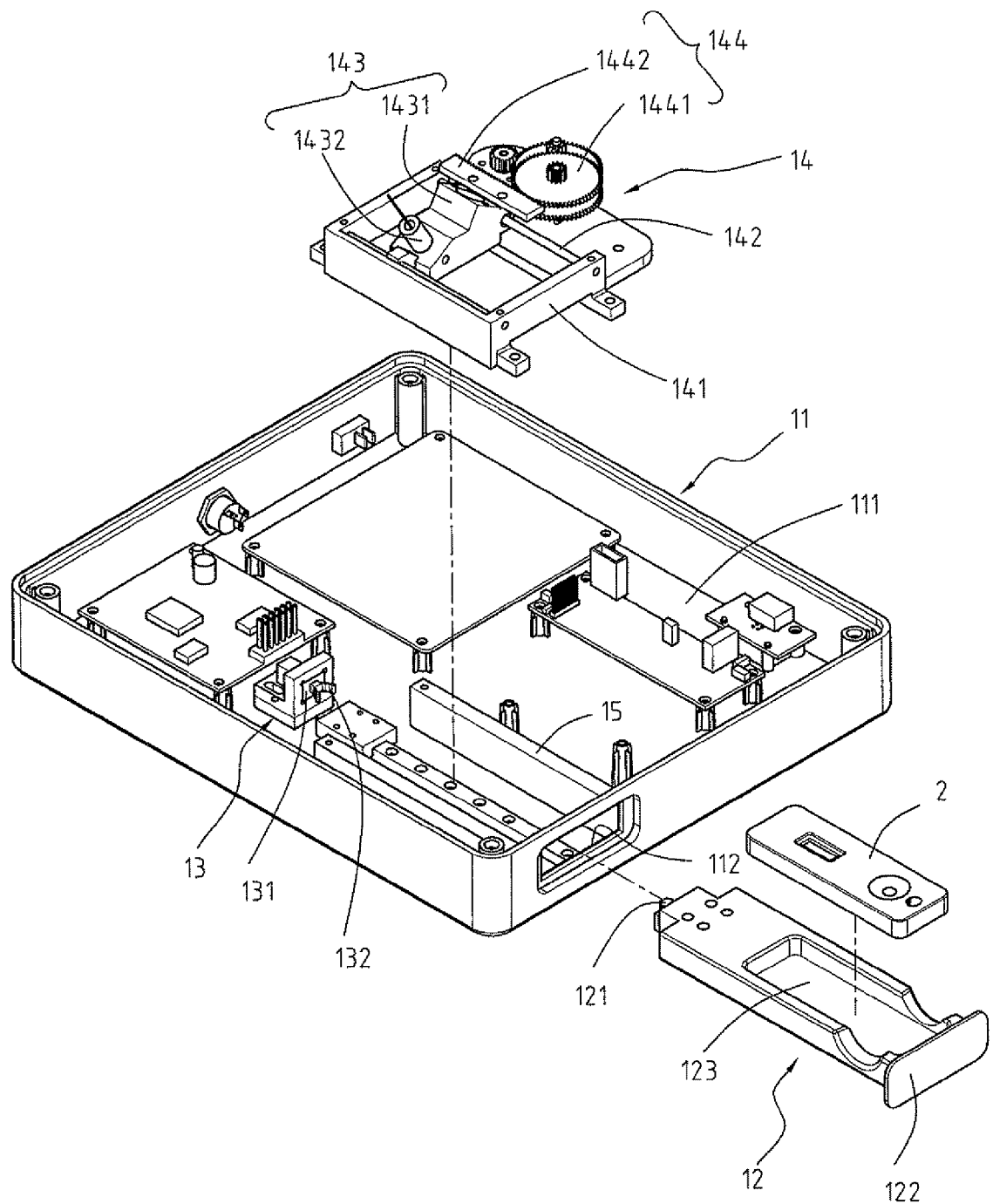
FIG. 2 is a partially exploded perspective view of the automatic physiological assay device in FIG. 1.
Figure 3:
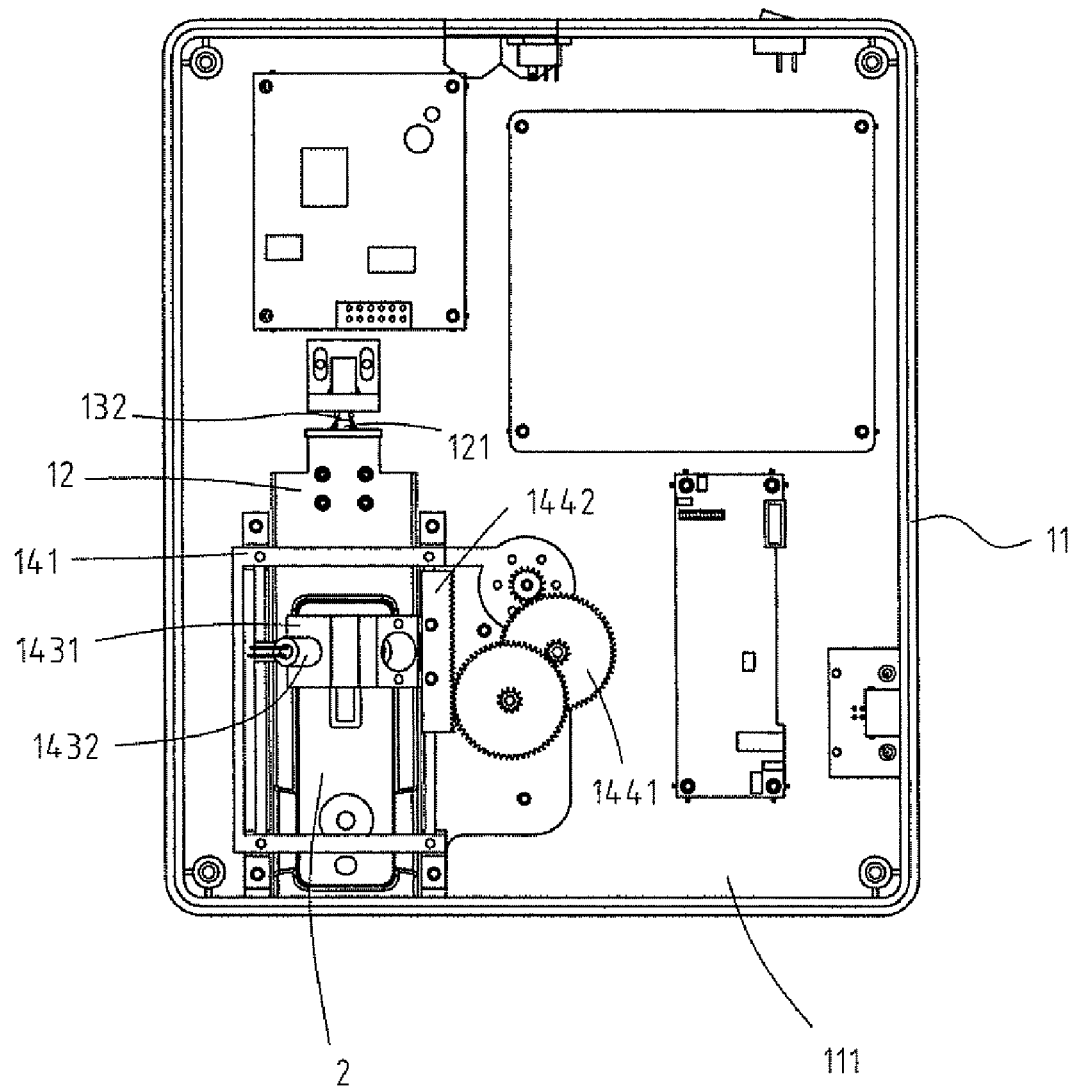
FIG. 3 is a top view of the automatic physiological assay device in FIG. 1.

With reference to FIGS. 1, 2 and 3, an automatic physiological assay device in accordance with the present invention analyzes light reflected from a biomedical detector, prevents ambient light interference and comprises a chassis (11), an assay device connector assembly (12), an assay device (2) and a light detecting device (14).

The chassis (11) comprises a closed bottom, multiple sidewalls, an inner cavity (111), an open top and a removable top cover (not shown). The sidewalls are mounted on and protrude up from the closed bottom. Adjacent sidewalls are connected to each other. Each sidewall has a top edge. One sidewall has an opening (112). The opening (112) has two ends.

The inner cavity (111) is formed inside the sidewalls, communicates with the opening (112) in the sidewall and comprises two guides (15) and a connector socket (13). The guides (15) are mounted parallel to each other on the closed bottom and abut the sidewall respectively outside the two ends of the opening (112), and each guide (15) has a top edge.

Figure 5:
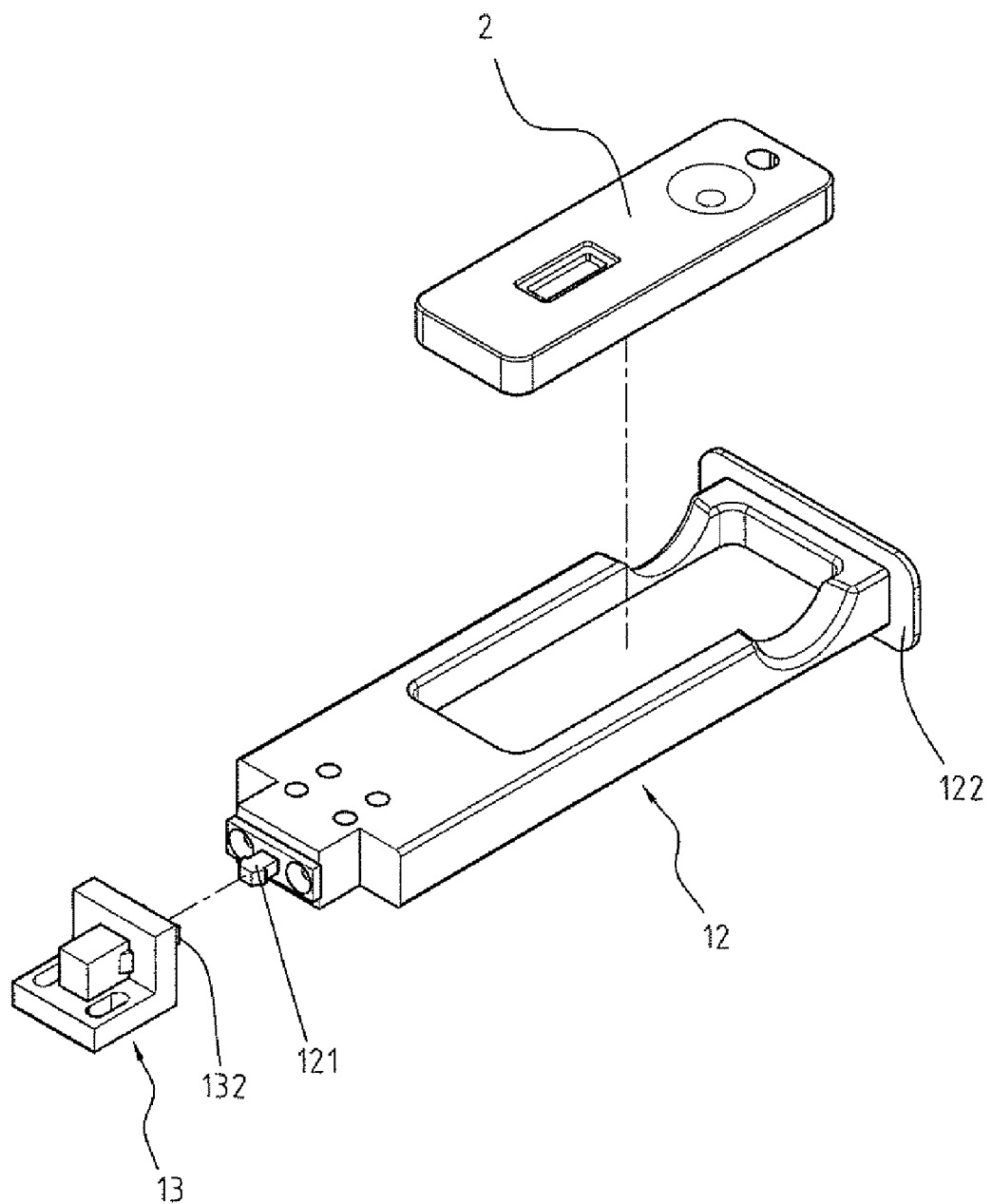
FIG. 5 is an exploded perspective view of a connector socket, an assay device and an assay device connector assembly in accordance with the present invention.

With further reference to FIG. 5, the connector socket (13) is mounted on the closed bottom between the guides (15), faces the opening (112) and comprises a base, a restricting frame (131), a resilient center and a claw (132). The base has a top surface, an outer edge and an inner edge. The outer edge faces and is parallel to the opening (112) in the sidewall. The restricting frame (131) is formed flush with the outer edge of and protrudes up from the base and has a central opening. The resilient center is formed on the top surface of the base flush with the inner edge, protrudes up from the base, protrudes forward movably into the central opening and has an outer end. The claw (132) is attached to the outer end of the resilient center and has two hooks. The hooks abut and are pressed together by the restricting frame (131) when the resilient center is pressed toward the inner edge of the base.

Figure 4:
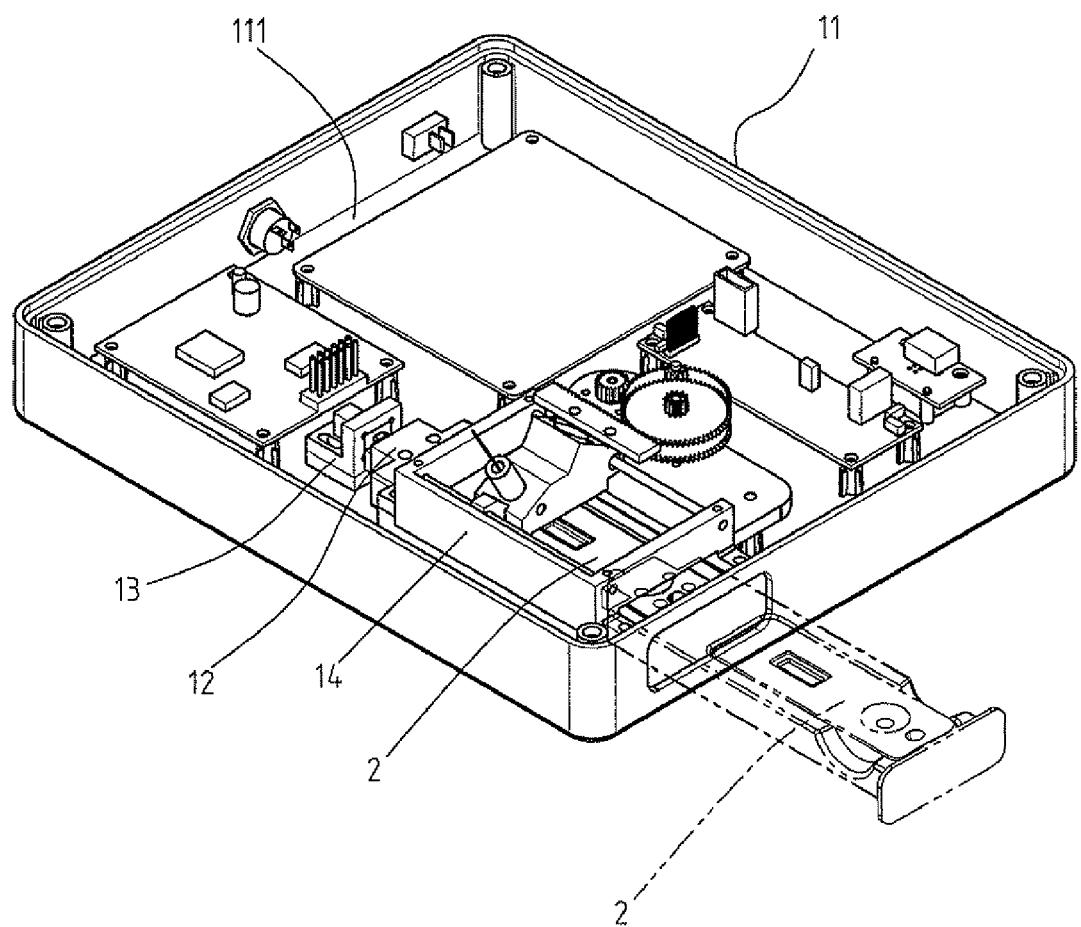
FIG. 4 is an operational perspective view of the automatic physiological assay device in FIG. 1.

With further reference to FIG. 4, the assay device connector assembly (12) is mounted slidably through the opening (112) in the sidewall and into the inner cavity (111), connects to the connector socket (13) and comprises an inner end, an outer end, an upper surface, two sides, a knob (121), an end cover (122) and a recess (123). The knob (121) is formed on, protrudes longitudinally from the inner end and is engaged by the hooks on the claw (132) when the knob (121) presses the resilient center. The cover (122) is mounted on the outer end, seals the opening (112) in the sidewall and keeps ambient light from entering the assay device connector assembly (12) when the assay device connector assembly (12) is pushed into the inner cavity (111). The recess (123) is formed in the upper surface adjacent to the outer end.

The assay device (2) has a top surface and is mounted removably in the recess (123) in the assay device connector assembly (12) and longitudinally holds the biomedical detector visibly on the top surface.

The light detecting device (14) is mounted in the inner cavity (111) on the guides (15) above the assay device connector assembly (12) and longitudinally holds the biomedical detector visible on the top surface and comprises a light detector base (141), two mounting rails (142), a light detector assembly (143) and a gear assembly (144). The light detector base (141) is mounted on the top edges of the guides (15) above the assay device connector assembly (12). The mounting rails (142) are mounted on the light detector base (141) parallel to each other and longitudinally to the assay device connector assembly (12). The light detector assembly (143) is mounted movably on the mounting rails (142) and comprises a moving base (1431), a light source and a light detector (1432). The moving base (1431) is mounted movably on the mounting rails (142) and has two sides. The light source is mounted in one side of the moving base (1431) to provide light. The light detector (1432) is mounted in the other side of the moving base (1431) to detect light reflected from the biomedical detector and may be a photo diode, a charge-coupled device (CCD) or a complementary metal oxide semiconductor (CMOS). The gear assembly (144) is mounted beside the light detector base (141) and comprises at least one gear (1441) and a rack (1442). The gear (1441) is driven by a motor. The rack (1442) engages and moves with the gear (1441) and connects to the moving base (1431) to make the light detector (1432) move back and forth to detect light.

A person knowledgeable in the art will understand that various changes could be made without departing from the broad spirit and scope of the invention. The foregoing description is intended to illustrate the present invention and not to limit the scope of the present invention.

What is claimed is:

1. An automatic physiological assay device analyzing light reflected from a biomedical detector, preventing ambient light interference and comprising a chassis comprising
    a closed bottom;
    multiple sidewalls being mounted on and protruding up from the closed bottom; adjacent sidewalls being connected to each other, each sidewall having a top edge, and one sidewall having an opening with two ends;
    an inner cavity being formed inside the sidewalls, communicating with the opening in the sidewall and comprising
        two guides being mounted parallel to each other on the closed bottom and abutting the sidewall respectively outside the two ends of the opening, and each guide having a top edge; and
        a connector socket being mounted on the closed bottom between the guides, facing the opening and comprises
            a base having
                a top surface;
                an outer edge facing and being parallel to the opening in the sidewall; and
                an inner edge;
            a restricting frame being formed flush with the outer edge of and protruding up from the base and having a central opening;
            a resilient center being formed on the top surface of the base flush with the inner edge, protruding up from the base, protruding forward movably into the central opening and has an outer end; and
            a claw being attached to the outer end of the resilient center and having two hooks abutting the restricting frame;
        an open top; and
        a removable top cover opening being connected to the inner space;
    an assay device connector assembly being mounted slidably through the opening in the sidewall and into the inner cavity, connecting to the connector socket and comprising
        an inner end;
        an outer end;
        an upper surface;
        two sides;
        a knob being mounted on and protruding longitudinally from the inner end and being engaged by the hooks on the claw when the knob presses the resilient center;
        an end cover being mounted on the outer end, sealing the opening in the sidewall and keeping ambient light from entering the assay device connector when the assay device connector assembly is pushed into the inner cavity; and
        a recess being formed in the upper surface adjacent to the outer end;
    an assay device having a top surface and being mounted removably in the recess in the assay device connector assembly and longitudinally holds the biomedical detector visibly on the top surface; and
    a light detecting device being mounted in the inner cavity, on the guides above the assay device connector assembly, longitudinally holding the biomedical detector visible on the top surface and comprising
        a light detector base being mounted on the top edges of the guides above the assay device holder;
        two mounting rails being mounted on the light detector base parallel to each other and longitudinally to the assay device connector assembly;
        a light detector assembly being mounted movably on the mounting rails and comprising
            a moving base being mounted movably on the shafts and having two sides;
            a light source being mounted in the one side of the moving base; and
            a light detector being mounted in the other side of the moving base to detect light reflected from the biomedical detector; and
        a gear assembly being mounted beside the light detector base and comprising
            at least one gear being driven by a motor; and
            a rack being engaging and moving with the gear and connecting to the moving base.

2. The automatic physiological assay device as claimed as claim 1, wherein the light detector is a photo diode.

3. The automatic physiological assay device as claimed as claim 1, wherein the light detector is a charge-coupled device (CCD).

4. The automatic physiological assay device as claimed as claim 1, wherein the light detector is a complementary metal oxide semiconductor (CMOS).

* * * * *